United States Patent
Buese et al.

[11] Patent Number: 5,914,420
[45] Date of Patent: Jun. 22, 1999

[54] PERFLUORINATED ORGANO SUBSTITUTED CYYLOSILOXANES AND COPOLYMERS PREPARED FROM THESE CYCLOSILOXAHES

[75] Inventors: Mark A. Buese, Gainesville; John Scott Shaffer, Fruit Cove, both of Fla.

[73] Assignee: PCR, Inc., Gainesville, Fla.

[21] Appl. No.: 09/086,649

[22] Filed: May 29, 1998

[51] Int. Cl.⁶ .................................. C07F 7/08; C07F 7/10
[52] U.S. Cl. ..................... 556/448; 556/419; 556/425; 556/439; 556/440; 556/460; 528/14; 528/21; 528/23
[58] Field of Search ..................... 556/448, 419, 556/460, 425, 439, 440; 528/14, 21, 23

[56] References Cited

U.S. PATENT DOCUMENTS

| | | | |
|---|---|---|---|
| 3,876,677 | 4/1975 | Wu | 556/448 |
| 4,247,674 | 1/1981 | Koshar et al. | 528/21 |
| 4,898,958 | 2/1990 | Kishita et al. | 556/448 |
| 4,968,828 | 11/1990 | Yamamoto | 556/448 |
| 4,996,344 | 2/1991 | Inomata et al. | 556/448 |
| 5,099,053 | 3/1992 | Takaoka et al. | 556/448 |
| 5,118,775 | 6/1992 | Inomata et al. | 528/12 |
| 5,202,453 | 4/1993 | Kishita et al. | 556/448 |
| 5,210,253 | 5/1993 | Kinami et al. | 556/448 |
| 5,233,071 | 8/1993 | Wilczek | 556/479 |
| 5,247,116 | 9/1993 | Buese et al. | 556/460 |
| 5,300,613 | 4/1994 | Kishita et al. | 528/26 |
| 5,374,760 | 12/1994 | Kobayashi | 556/448 |
| 5,412,135 | 5/1995 | Fukuda et al. | 556/448 |
| 5,548,054 | 8/1996 | Okada et al. | 528/25 |
| 5,670,689 | 9/1997 | Allandrieu et al. | 556/460 |
| 5,700,898 | 12/1997 | Okada et al. | 556/448 X |

Primary Examiner—Paul F. Shaver
Attorney, Agent, or Firm—Hedman, Gibson & Costigan, P.C.

[57] ABSTRACT

Compositions of unstrained perfluorinated organo substituted cyclosiloxanes of formula (I):

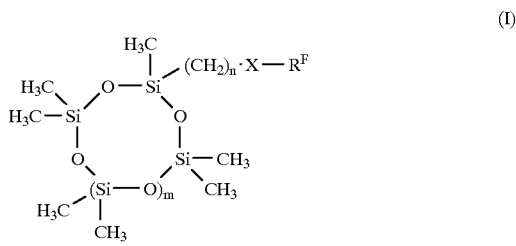

wherein m is an integer of 1 to 12; n is an integer of 1 to 4; X is a divalent radical which may include O, NH, N(CH$_3$), OC(O), NHC(O), N(CH$_3$)C(O)CH$_2$; and R$^F$ is a perfluorinated straight chain or branched chain monovalent alkyl radical of 1 to 25 carbon atoms; or R$^F$ is a perfluorinated ether radical of the general formula (II):

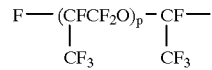

wherein p is an integer of 1 to 10 are described, along with copolymer compositions prepared from these cyclopolysiloxanes and from mixtures of these cyclosiloxanes and other siloxanes.

40 Claims, No Drawings

PERFLUORINATED ORGANO SUBSTITUTED CYYLOSILOXANES AND COPOLYMERS PREPARED FROM THESE CYCLOSILOXAHES

FIELD OF THE INVENTION

The present invention relates to the preparation of cyclosiloxanes with one perfluorinated substituent and their ring-opening polymerization into silicone copolymers.

BACKGROUND OF THE INVENTION

One of the most important methods of preparing silicone polymers and copolymers is via ring-opening polymerization. Most commonly it is carried out by the polymerization of unstrained cyclosiloxanes, generally cyclic tetramers or pentamers, where no heat is generated upon polymerization. Typically the polymer constitutes up to approximately 90 percent of the resulting equilibrium mixture depending upon the substituents on the cyclosiloxane, the degree of polymerization achieved, and the amount of any solvent used in the polymerization. The amount of cyclosiloxanes that have been observed in equilibrium with many silicone polymers is described in Siloxane Polymers, Chapter 3, S. J. Clarson and J. A. Semlyen, ed., Ellis Horwood - PTR Rentis Hall, Englewood Cliffs, N.J., 1993. Polymerization can also be carried out with cyclic trimers. Cyclic trimers are strained and the polymerization is exothermic. Cyclic trimers are generally more difficult to prepare than cyclic tetramers and pentamers.

The most common fluorinated silicone is prepared by the ring-opening polymerization of 1,3,5-tris-(3,3,3-trifluoropropyl)-1,3,5-trimethylcyclotrisiloxane. The weight percent of the fluorocarbon portion of the cyclosiloxane and its resulting homopolymer is 44% by weight. The exothermic polymerization is driven due to the ring strain that is released upon the opening of the cyclic trimer. The polymerization must be stopped immediately after high polymer has formed, otherwise the polymer reverts to a mixture of cyclics, primarily the unstrained tetramer and pentamer which together constitute about 90% by weight of the cyclic mixture.

U.S. Pat. No. 5,202,453 describes a strained cyclotrisiloxane with a single fluorinated organic substitutent. This compound was prepared in a two step process from a 1H,1H,2H-vinyl terminated oligomer of hexafluoropropene oxide with a combined yield of approximately 50% based upon the moles of oligomer used. Though not demonstrated in the patent, it was suggested to be ring-opening polymerizable in the presence of alkaline or acid catalysts, presumably under conditions similar to those used for the polymerization of 1,3,5-tris-(3,3,3-trifluoropropyl)-1,3,5-trimethylcyclotrisiloxane.

Unstrained cyclosiloxanes with one or two large substituents on each Si atom typically are difficult to polymerize as the magnitude of a cyclosiloxane's equilibrium constant increases relative to that of a cyclosiloxane with smaller substituents, while at the same time the maximum concentration of the Si—O bond decreases as the size of the substituent increases. These factors result in a very high proportion of cyclosiloxanes at equilibrium as in the case of 1,3,5-tris-(3,3,3-trifluoropropyl)-1,3,5-trimethylcyclotrisiloxane. Because of this problem, it is common to prepare a silicone polymer with a small reactive group, often a hydrogen substituent, on the backbone. The hydrosilation of an olefin with a Si—H containing compound is frequently used to prepare organically substituted siloxanes. This hydrosilation is often difficult to perform if the solubility of the group to be substituted on the siloxane backbone is a low in the Si—H containing silicone polymer. Often a Si—H containing polymer contains sites where the Si—H has undergone hydrolysis to Si—OH during its preparation, storage, or during the hydrosilation reaction if water is present. Such units can permit the formation of branches or gels during the hydrosilation reaction. Perfluorinated organic molecules often display very low miscibility in silicone polymers. Hydrosilation reactions often do not proceed to complete conversion of the olefin or the silane reactants. For these reasons it is difficult to achieve a perfluorinated organic substituted silicone polymer by modification of a functional silicone polymer without defects in the structure due to incomplete reaction or defects from the starting Si—H containing polymer.

U.S. Pat. No. 5,247,116 describes a method where unstrained cyclosiloxanes with a single functional group can be prepared and subsequently isolated. This functional group may be transformed in a variety of fashions such that a single perfluorinated organic moiety may be introduced to a cyclosiloxane ring. The advantage of such a cyclosiloxane is that the Si—O bond concentration can be significantly higher than that of cyclosiloxane with a perfluorinated organic substituent at every Si atom, for an equivalent molecular weight of the cyclosiloxane. Furthermore, the equilibrium cyclization constants for the majority of the resulting cyclosiloxanes remain close to that of cyclodimethylsiloxanes. This results in a much greater fraction of linear siloxanes at equilibrium upon polymerization of the cyclosiloxane even though the starting cyclosiloxane is unstrained.

SUMMARY OF THE PRESENT INVENTION

One object of the present invention is to provide unstrained polymerizable cyclosiloxanes that have one substituent that contains a perfluorinated organic moiety whose structure is given by the general formula (I):

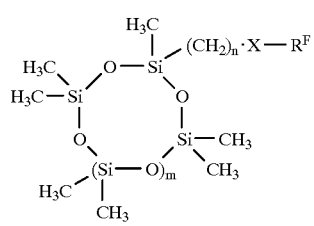

(I)

wherein m is an integer of 1 to 12; n is an integer of 1 to 4; X is a divalent radical which may include O, NH, N(CH$_3$), OC(O), NHC(O), N(CH$_3$)C(O) and CH$_2$; and R$^F$ is a perfluorinated straight chain or branched chain monovalent alkyl radical of 1 to 25 carbon atoms; or R$^F$ is a perfluorinated ether radical of the general formula (II):

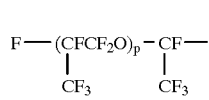

(II)

wherein p is an integer of 1 to 10.

It is an object of the invention to prepare copolymers that result from the ring-opening polymerization of the cyclosiloxanes of formula (I) to give a copolymer of the general formula (III):

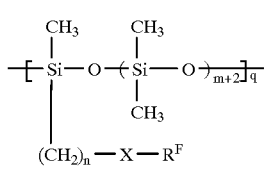

(III)

wherein m, n, X, and $R^F$ are defined as in formula (I); and q may be 2 to 1,000,000.

It is an object of the present invention to prepare copolymers from the cyclosiloxanes of formula (I) and cyclodimethylsiloxanes and/or polydimethylsiloxanes such that the resulting copolymer contains a lesser proportion of fluorinated siloxane groups than the cyclosiloxanes of formula (I).

It is an object of the present invention to prepare fluorinated silicones which contain in addition to the siloxy repeating units present in the cyclosiloxanes of formula (I) other siloxy repeating units which include, but are not exclusive to, hydrogenmethylsiloxy, methylvinylsiloxy, methylphenylsiloxy, (cyanoethyl)methylsiloxy, (aminopropyl)methylsiloxy, (hydroxypropyl)methylsiloxy, and (trifluoropropyl)methylsiloxy units. These units may be incorporated by the addition of the appropriate cyclosiloxane which contains one or more of these groups.

It is an object of the present invention to prepare copolymers from the cyclosiloxanes of the formula (I) and, optionally, other cyclosiloxanes, where the degree of polymerization is controlled by end-capping. This is achieved by equilibrating the appropriate cyclosiloxanes with a disiloxane or the disiloxane's equivalent incorporated into a small polysiloxane. A wide variety of disiloxanes and/or their equivalents in polysiloxanes are known which include, but are not exclusive to, hexamethyldisiloxane, 1,1,3,3-tetramethyldisiloxane, 1,3-divinyl-1,1,3,3-tetramethyldisiloxane, 1,3-di-(3-aminopropyl)-1,1,3,3-tetramethyldisiloxane, 1,3-di(3-hydroxypropyl)-1,1,3,3-tetramethyldisiloxane, 1,3-diphenyl-1,1,3,3-tetramethyldisiloxane, 1,3-di-(3-chloropropyl-1,1,3,3-tetramethyldisiloxane, and 1,3-di-(3-methacryloxypropyl)-1,1,3,3-tetramethyldisiloxane, and mixtures of any of the foregoing.

DETAILED DESCRIPTION OF THE PRESENT INVENTION

The unstrained polymerizable cyclosiloxanes of the present invention are those which have methyl groups at all but one site for substituents. That site contains a perfluorinated organic moiety that may have a variety of molecular weights and functional groups connecting the moiety to the cyclosiloxane ring.

The cyclosiloxanes have the general formula (I). The cyclosiloxanes may be produced by a hydrosilation reaction between a mono Si—H containing cyclodimethylsiloxane, such as heptamethylcyclotetrasiloxane or nonamethylcyclopentasiloxane, and a 1H,1H,2H-vinyl substituted fluorinated organic molecule.

The cyclosiloxane of formula (I) may be produced by reacting an oligomer of hexafluoropropeneoxide of the structure:

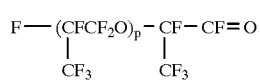

(IV)

wherein p is an integer of from 1 to 10, with an organic molecule that contains an amine or alcohol and a terminal vinyl group followed by hydrosilation between that amide or ester with a mono Si—H containing cyclodimethyldisiloxane. Alternately, the mono Si—H containing cyclodimethylsiloxane may undergo hydrosilation with an amine, such as allyl amine or N-methylallyl amine, or an alcohol, such as allyl alcohol, with a terminal vinyl group followed by its reaction with an oligomer of hexafluoropropene oxide of formula (IV). In some cases, the ester that would result from the reaction between the oligomer of hexafluoropropene oxide of formula (IV) and methanol or ethanol may be used in an amidation or in a transesterification reaction to yield the cyclosiloxane of formula (I).

The cyclosiloxanes of formula (I) may be polymerized using an acid or alkaline catalyst in a manner typical of unstrained cyclosiloxanes to a mixture of linear copolymer and cyclic oligomers. The choice of catalyst will be dependent upon the nature of the group X in the cyclosiloxane of formula (I) as is known to those skilled in the art. The linear copolymer may be separated from the cyclic oligomers by extraction with a hydrocarbon. The size of the hydrocarbon may vary depending upon the size of the perfluorinated organic moiety. In general the hydrocarbon will be less than 10 carbons in the chain such that it is sufficiently volatile to be easily removed from the extracted cyclosiloxanes and the copolymer. The resulting copolymer will have the general formula (III). The extracted cyclic oligomers may be repolymerized in like manner to the cyclosiloxanes of formula (I) from whose polymerization mixture it was extracted. The extracted cyclosiloxanes will be of the formula (V):

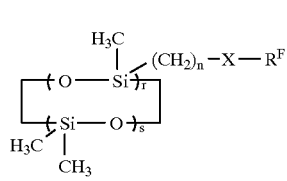

(V)

wherein n, X, and $R^F$ are defined as in formula (I), and r+s=t and t is 4 to 20 and r is 1 to t.

The degree of polymerization can be controlled by the amount of catalyst used and, to a greater extent, the presence of any chain capping agent which may be included in the polymerization mixture. Capping agents which may be used are typically disiloxanes of the formula (VI):

R—Si(CH$_3$)$_2$OSi(CH$_3$)$_2$—R          (VI)

wherein R is H, methyl, ethyl, phenyl, vinyl, hydroxypropyl, aminopropyl, or any other functional hydrocarbon radical. The choice of the disiloxane will depend upon the specific formulation of the resulting copolymer chosen for the final application of the copolymer as is known to those skilled in the art.

The cyclosiloxane of formula (I) may be copolymerized with a wide variety of cyclosiloxanes and linear siloxanes. Cyclodimethylsiloxanes such as octamethylcyclotetrasiloxane or decamethylcyclopentasiloxane may be used to produce a copolymer where the ratio of dimethylsiloxy groups to methylperfluoroorganosiloxy group is a value greater than three. Cyclosiloxanes with functional groups can be incorporated to permit specific processing or impart specific properties to the copolymer depending upon the final application of the copolymer as is known to those skilled in the art. Cyclosiloxanes which may be copolymerized with the cyclosiloxane of formula (I) include, but are not exclusive to, those which contain hydrogenmethylsiloxy, methylvinylsiloxy, methylphenylsiloxy, (cyanoethyl) methylsiloxy, (aminopropyl)methylsiloxy, (hydroxypropyl) methylsiloxy, (acryloxypropyl)methylsiloxy, and (methacryloxypropyl)methylsiloxy repeating units.

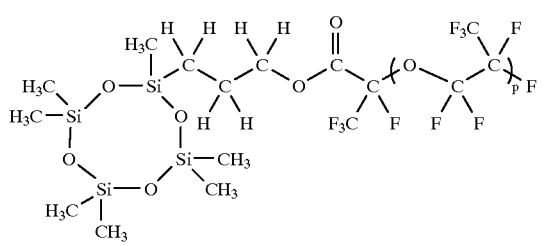

(VII)

DESCRIPTION OF THE PREFERRED EMBODIMENTS

The practice of the present invention is illustrated by the following non-limiting examples. These examples are provided for illustrative purposes only and should not be construed to limit the scope of the claims in any manner whatsoever.

EXAMPLE 1

A 50 mL round bottom flask equipped with a magnetic stirring bar and an addition funnel was charged with 7.7 g of 98% (3-hydroxypropyl)heptamethylcyclotetrasiloxane (22 mmoles) and 2.3 g of triethylamine (23 mmoles). The mixture was stirred and 15.0 g of 97% perfluoro-2,5,8-trimethyl-3,6,9-trioxadodecanoyl fluoride (21.9 mmoles) was added dropwise. After complete addition of the acid fluoride a gas chromatographic analysis indicated that essentially all of the acid fluoride and most of the cyclosiloxane were consumed with predominately the formation of one product. A 25 mL portion of dilute hydrochloric acid was added to the flask and the two phase mixture was transferred into a separatory funnel and the aqueous layer separated from the siloxane layer. The siloxane layer was washed with two 25 mL portions of water and the siloxane layer was transferred into a 50 mL round bottom flask and distilled at 110° C. and 0.3 mm Hg to yield a fraction of 14.7 g (66% yield) of 97% [3-(perfluoro-2,5,8-trimethyl-3,6,9-trioxadodecanoyl)oxypropyl]heptamethylcyclotetrasiloxane (14.3 mmoles), which corresponds to formula (I) wherein m is 1, n is 3, X is OC(O), and $R^F$ is given by formula (II) wherein p is 3, or more specifically as shown in formula (VII) below wherein p is 3. The product was analyzed by spectroscopy with the following results: $^1$H NMR 400 MHz, CDCl$_3$: d 0.1 (s 21 H), 0.6 (t 2 H), 1.8 (p 2 H), 4.4 (m 2 H); $^{19}$F NMR 376 MHz, CDCl$_3$: d −81 (CF$_3$), −82 (CF$_3$), −83 (CF$_3$), −85 (CF$_3$), −130 (CF$_2$), −132 (CF$_2$), −144 (CF); IR (neat liquid on NaCl): cm$^{-1}$: 2970 (m), 1780 (s), 1245 (vs), 1200 (s), 1145 (s), 1070 (vs), 995 (s), 970 (s), 810 (vs), 750 (m).

EXAMPLE 2

A 50 mL round bottom flask equipped with a magnetic stirring bar and an addition funnel was charged with 6.2 g of 98% (3-hydroxypropyl)heptamethylcyclotetrasiloxane (18 mmoles) and 1.8 g of triethylamine (18 mmoles). The mixture was stirred and 15.0 g of 95% perfluoro-2,5,8,11-tetramethyl-3,6,9,12-tetraoxapentadecanoyl fluoride (17 mmoles) was added dropwise. After complete addition of the acid fluoride a gas chromatographic analysis indicated that essentially all of the acid fluoride and most of the cyclosiloxane were consumed with predominately the formation of one product. A 25 mL portion of dilute hydrochloric acid was added to the flask and the two phase mixture was transferred into a separatory funnel and the aqueous layer was separated from the siloxane layer. The siloxane layer was washed with two 25 mL portions of water and the siloxane layer was transferred into a 50 mL round bottom flask and distilled at 118–28° C. and 0.05 mmHg to yield a fraction of 14.0 g (71% yield) of 99% [3-(perfluoro-2,5,8,11-tetramethyl-3,6,9,12-tetraoxapentadecan-oyl) oxypropyl]heptamethylcyclotetrasiloxane (12.2 mmoles), which corresponds to formula (I) wherein m is 1, n is 3, X is OC(O), and $R^F$ is given by formula (II) wherein p is 4, or more specifically as shown in formula (VII) wherein p=4. The product was analyzed by spectroscopy with the following results: $^1$H NMR 400 MHz, CDCl$_3$: d 0.1 (s 21 H), 0.6 (t 2 H), 1.8 (p 2 H), 4.4 (m 2 H); IR (neat liquid on NaCl): cm 2970 (m), 1780 (s), 1245 (vs), 1200 (s), 1145 (s), 1070 (vs), 995 (s), 970 (s), 810 (vs), 750 (m).

EXAMPLE 3

A 50 mL round bottom flask equipped with a magnetic stirring bar and an addition funnel was charged with 5.1 g of 98% (3-hydroxypropyl)heptamethylcyclotetrasiloxane (15 mmoles) and 1.5 g of triethylamine (15 mmoles). The mixture was stirred and 15.0 g of 92% perfluoro-2,5,8,11, 14-pentamethyl-3,6,9,12,15-tetraoxaoctadecanoyl fluoride (14 mmoles) was added dropwise. After complete addition of the acid fluoride a gas chromatographic analysis indicated that essentially all of the acid fluoride and most of the cyclosiloxane were consumed with predominately the formation of one product. A 25 mL portion of dilute hydrochloric acid was added to the flask and the two phase mixture was transferred into a separatory funnel and the aqueous layer was separated from the siloxane layer. The siloxane layer was washed with two 25 mL portions of water and the siloxane layer was transferred into a 50 mL round bottom flask and distilled at 128–38° C. and 0.05 mmHg to yield a fraction of 13.0 g (71% yield) of >99% [3-(perfluoro-2,5,8,11,14-pentamethyl-3,6,9,12,15-pentaoxaocta-decanoyl)oxypropyl]heptamethylcyclotetrasiloxane (14.1 mmoles), which corresponds to formula (I) wherein m is 1, n is 3, X is OC(O), and $R^F$ is given by formula (II) wherein p is 5, or more specifically as shown in formula (VII) wherein p=5. The product was analyzed by spectroscopy with the following results: $^1$H NMR 400 MHz, CDCl$_3$: d 0.1 (s 21 H), 0.6 (t 2 H), 1.8 (p 2 H), 4.4 (m 2 H); IR (neat liquid on NaCl): cm$^{-1}$: 2970 (m), 1780 (s), 1245 (vs), 1200 (s), 1145 (s), 1070 (vs), 995 (s), 970 (s), 810 (vs), 750 (m).

EXAMPLE 4

Five different 10 mL round bottom flasks equipped with magnetic stirring bars and fitted with rubber septa were charged with 0.5 g of 98% (3-hydroxypropyl) heptamethylcyclotetrasiloxane (1.5 mmoles) and into 4 of the flasks was added a portion of an inorganic base as indicated in Table 1. All the bases were used as received and were in excess of 98% purity. The mixture was stirred and 1.2 g of 95% perfluoro-2,5,8,11-tetramethyl-3,6,9,12-tetraoxapentadecanoyl fluoride (1.4 mmoles) was added dropwise via a 3 mL syringe with a 25 G needle through the septa with an additional 25 G needle placed in the septa to assure that any pressure generated could be released. After complete addition of the acid fluoride a gas chromatographic analysis was run. The differences observed in the reaction mixtures resulting from the use of these different bases are indicated in Table 1.

| Base | Mass in g | mequivalents | Ratio* |
| --- | --- | --- | --- |
| None | | | 16.2 |
| CaH$_2$ | 0.08 | 1.9 | 19.7 |
| MgSO$_4$ | 0.21 | 1.7 | 13.3 |
| MgO | 0.07 | 1.7 | 14.0 |
| K$_2$HPO$_4$ | 0.31 | 1.8 | 68.0 |

EXAMPLE 5

A 3-necked 250 mL round bottom flask equipped with a magnetic stirring bar, a temperature probe, and an addition funnel was charged with 34.6 g of 99% (3-hydroxypropyl) heptamethylcyclotetrasiloxane (101 mmoles) and 17.0 g of K$_2$HPO$_4$ (97.6 mequivalents). The mixture was stirred and 87.6 g of hexafluoropropeneoxide oligomer acid fluoride with an average degree of polymerization of 4.4 (119 mmoles) was added dropwise at a rate such that the temperature did not exceed 40° C. The contents of the pot was placed in a funnel attached to a filter flask with a 1 micron filter in line and collected in the flask when vacuum was applied to the flask. The 100.6 g of liquid in the filter was transferred into a 250 mL round bottom flask and distilled at 51–128° C. and 0.05 to 0.25 mmHg to yield a fraction of 68 g (57% yield) of [3-(oligohexafluoropropeneoxide-oyl)oxypropyl]heptamethylcyclotetrasiloxane (12.2 mmoles), which corresponds to formula (I) wherein m is 1, n is 3, X is OC(O), and $R^F$ is given by formula (II) wherein p is 4.1, or more specifically as shown in formula (VII) wherein p averages 4.1, as determined by $^{19}$F NMR spectroscopy from the integration ratio's of CF$_3$ signals, and by gas chromatography assuming a relative response of individual homologues proportional to their mass and retention times of homologues determined from monodispersed standards from examples 1 through 3, with a dispersivity index, $X_w/X_n$, of 1.1. The product was analyzed by spectroscopy with the following results: $^1$H NMR 400 MHz, CDCl$_3$: d 0.1 (s 21 H), 0.6 (t 2 H), 1.8 (p 2 H), 4.4 (m 2 H); F NMR 376 MHz, CDCl$_3$: d −81 (CF$_3$), −82 (CF$_3$), −83 (CF$_3$), −85 (CF$_3$), −130 (CF$_2$), −132 (CF$_2$), −145 (CF); IR (neat liquid on NaCl): cm$^{-1}$: 2970 (m), 1780 (s), 1245 (vs), 1200 (s), 1145 (s), 1070 (vs), 995 (s), 970 (s), 810 (vs), 750 (m).

EXAMPLE 6

A 25 mL round bottom flask equipped with a magnetic stirring bar and an addition funnel was charged with 4.0 g of (3-hydroxypropyl)heptamethylcyclotetrasiloxane (12 mmoles) and 1.0 g of pyridine (13 mmoles). The mixture was stirred and 5.0 g of perfluorooctanoyl chloride (12 mmoles) was added dropwise. After complete addition of the acid fluoride a gas chromatographic analysis indicated that essentially all of the acid chloride and most of the cyclosiloxane were consumed with one product as 96.5% of the mixture. The contents of the flask were filtered using a 0.45 micron syringe filter into a 50 mL 1-necked round bottom flask. The solids in the flask were washed with 2.5 mL of pentane and this suspension added to the syringe and filtered into the 50 mL flask. The solids in the syringe were washed with an additional 2.5 mL of pentane and filtered into the 50 mL flask. The contents of the flask were distilled at 82° C. and 0.04 mmHg to yield a fraction of [3-(perfluorooctanoyl)oxypropyl]-heptamethylcyclotetrasiloxane which corresponds to formula (I) wherein m is 1, n is 3, X is OC(O), and $R^F$ is a perfluorinated straight chain monovalent alkyl radical of 7 carbons atoms, or more specifically as shown in formula (VIII) below.

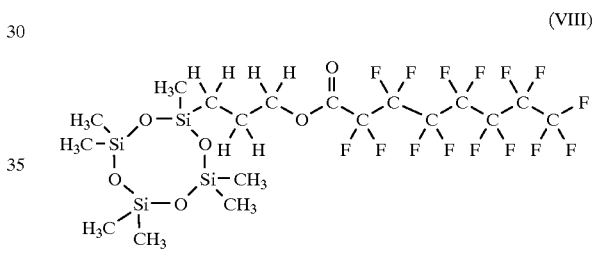

(VIII)

EXAMPLE 7

A 100 mL round bottom flask equipped with a magnetic stirring bar and an addition funnel was charged with 4.2 g of allyl alcohol (72 mmoles) and 9.5 g of anhydrous pyridine (120 mmoles). The mixture was stirred and 40 g of 97% perfluoro-2,5,8-trimethyl-3,6,9-trioxadodecanoyl fluoride (60 mmoles) was added dropwise. After complete addition of the acid fluoride, two phases were present. The stirring was stopped and the contents poured into a separatory funnel. A gas chromatographic analysis of the lower layer displayed no acid fluoride and very little allyl alcohol and the formation of one product in a significant quantity. The bottom ester layer was removed and the top layer discarded. The bottom ester layer was again placed in the separatory funnel and washed with a 20 mL portion of dilute hydrochloric acid. The ester was removed and subsequently washed with another 20 mL portion of dilute hydrochloric acid and then twice with 20 mL portions of water. The ester was transferred into a round bottom flask and distilled at 62–64° C. and 3 mmHg to yield a fraction of 29.0 g (69% yield) of >99% [3-perfluoro-2,5,8-trimethyl-3,6,9-trioxadodecan-oyl)oxy]-1-propene (41 mmoles).

A 3-necked 25 mL round bottom flask was equipped with a magnetic stirring bar, a condenser, and a temperature probe. The flask was charged with 10.0 g of >99% [3-(perfluoro-2,5,8-trimethyl-3,6,9-trioxadecan-oyl)oxy]-1- propene and 4.0 g of heptamethylcyclotetrasiloxane (14 mmoles). The mixture was heated to 80° C. and 10 μL of a Pt 1,3-divinyltetramethyldisiloxane complex in xylene (3% Pt) was added via a syringe. The temperature was increased. When the temperature exceeded 90° C. an exothermic reaction occurred with a rapid increase in temperature to 105° C. which soon cooled to below 100° C. After a gas chromatographic analysis indicated a low conversion, the temperature was increased to 100° C. and an additional 5 μL of the platinum catalyst solution was added to the mixture resulting in another exothermic reaction. The heating was then stopped and an additional gas chromatographic analysis indicated that although all of the reagents were consumed the desired product, [3-(perfluoro-2,5,8-trimethyl-3,6,9-trioxadodecan-oyl)oxypropyl]-heptamethylcyclotetrasiloxane, constituted only 18% of the mixture.

EXAMPLE 8

A 100 mL round bottom flask equipped with a magnetic stirring bar and an addition funnel was charged with 9.0 g of allyl amine (160 mmoles). The liquid was stirred and 40 g of 97% perfluoro-2,5,8-trimethyl-3,6,9-trioxadodecanoyl fluoride (60 mmoles) was added dropwise. Dilute hydrochloric acid was added to the flask and the two phase mixture was transferred into a separatory funnel and the aqueous layer separated from the amide layer. The amide layer was washed again with dilute hydrochloric acid and twice with water. The amide layer was transferred into a round bottom flask and distilled at 101° C. and 3 mmHg to yield a fraction of 21.6 (52% yield) of >99% N-allylperfluoro-2,5,8-trimethyl-3,6,9-trioxadodecanamide (31 mmoles).

A 3-necked 25 mL flask was equipped with a magnetic stirring bar, a condenser, and a temperature probe. The flask was charged with 10.0 g of >99% N-allyl-perfluoro-2,5,8-trimethyl-3,6,9-trioxadodecanamide (14 mmoles) and 4.0 g of heptamethylcyclotetrasiloxane (14 mmoles). The mixture was heated to 100° C. and 10 μL of a Pt 1,3-divinyltetramethyldisiloxane complex in xylene (3% Pt) was added via a syringe. An exothermic reaction occurred with a rapid increase in temperature to 147° C. which cooled after 10 minutes. A gas chromatographic analysis indicated high conversion to a single product. The contents of the flask were distilled at 116–20° C. and 0.04 mmHg to yield a fraction of 5.7 g (43% yield) of >99% N-(3-heptamethylcyclotetrasiloxan-yl)propylperfluoro-2,5,8-trimethyl-3,6,9-trioxadodecanamide (6 mmoles), which corresponds to formula (I) wherein m is 1, n is 3, X is NHC(O), and $R^F$ is given by formula (II) wherein p is 3, or more specifically as shown in formula (IX) below where R=H and p=3. The product was analyzed by spectroscopy with the following results: $^1$H NMR 400 MHz, CDCl$_3$: d 0.1 (m 21 H), 0.6 (t 2 H), 1.7 (p 2 H), 3.4 (m 2 H), 6.7 (s 1 H); IR (neat liquid on NaCl): cm$^{-1}$: 3460 (m), 2970 (m), 1705 (s), 1550 (m), 1310 (m), 1245 (vs), 1200 (s), 1150 (s), 1070 (vs), 995 (s), 970 (s), 810 (vs), 750 (m).

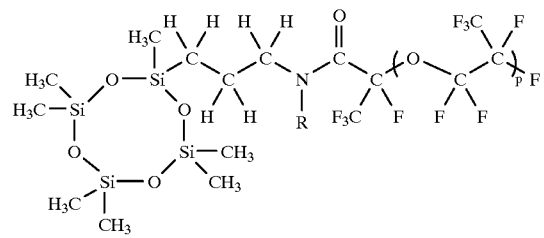

(IX)

EXAMPLE 9

A 100 mL round bottom flask equipped with a magnetic stirring bar and an addition funnel was charged with 5.0 g of N-methylallyl amine (70 mmoles). The liquid was stirred and 17.5 g of 97% perfluoro-2,5,8-trimethyl-3,6,9-trioxadodecanoyl fluoride (26 mmoles) was added dropwise. The reaction mixture was transferred into a separatory funnel and the amide layer was washed twice with dilute hydrochloric acid and once with water. The amide layer was transferred into a round bottom flask and distilled at 98° C. and 2.4 mmHg to yield a fraction of 14.3 g (77% yield) of >99% N-allyl-N-methyl-perfluoro-2,5,8-trimethyl-3,6,9-trioxadodecanamide (20 mmoles).

A 3-necked 25 mL round bottom flask was equipped with a magnetic stirring bar, a condenser, and a temperature probe. The flask was charged with 7.0 g of >99% N-allyl-N-methyl-perfluoro-2,5,8-trimethyl-3,6,9-trioxadodecanamide (10 mmoles) and 2.8 g of heptamethylcyclotetrasiloxane (10 mmoles). The mixture was heated to 106° C. and 10 μL of a Pt 1,3-divinyltetramethyldisiloxane complex in xylene (3% Pt) was added via a syringe. An exothermic reaction occurred with a rapid increase in temperature to 155° C. which cooled after 3 minutes. A gas chromatographic analysis indicated high conversion to a single product. The contents of the flask were distilled at 100–05° C. and 0.04 mmHg to yield a fraction of 5.2 g (53% yield) of >99% N-(3-heptamethylcyclotetrasiloxan-yl)propyl-N-methyl-perfluoro-2,5,8-trimethyl-3,6,9-trioxadodecanamide (5.2 mmoles), which corresponds to formula (I) wherein m is 1, n is 3, X is N(CH$_3$)C(O), and $R^F$ is given by formula (II) wherein p is 3, or more specifically as shown in formula (IX) where R=CH$_3$ and p=3. The product was analyzed by spectroscopy with the following results: $^1$H NMR 400 MHz, CDCl$_3$: d 0.1 (m 21 H), 0.5 (m 2 H), 1.7 (m 2 H), 3.1 (m 3 H), 3.5 (m 2 H); IR (neat liquid on NaCl): cm$^{-1}$:2970 (m), 1685 (s), 1410 (w), 1300 (m), 1245 (vs), 1200 (s), 1140 (m), 1080 (vs), 995 (s), 970 (s), 810 (vs), 750 (m).

EXAMPLE 10

A 500 mL round bottom flask equipped with a magnetic stirring bar, a temperature probe, a condenser, and an addition funnel was charged with 11.0 g of allyl amine (193 mmoles) and 15 g of pyridine (190 mmoles). The liquid was stirred and 150 g of hexafluoropropeneoxide oligomer acid fluoride, with a degree of polymerization of 4.4 (205 mmoles) was added dropwise. The contents of the flask were transferred to a separatory funnel and washed twice with dilute hydrochloric acid and subsequently washed twice with water. The amide layer was transferred into a round bottom flask. The product was distilled at 95–190° C. and 5.1 mmHg to yield a fraction of 125 g (84% yield) of N-allyloligohexafluoropropeneoxide-oyl amide.

A 3-necked 250 mL round bottom flask was equipped with a magnetic stirring bar, a condenser, and a temperature probe. The flask was charged with 5.0 g of N-allyl-oligohexafluoropropeneoxide-oyl amide (6.5 mmoles) and 30 g of heptamethylcyclotetrasiloxane (106 mmoles). The mixture was heated to 100° C. and 30 μL of a Pt 1,3-divinyltetramethyldisiloxane complex (3% Pt) was added via a syringe. An additional 70 g of N-allyloligohexafluoropropeneoxide-oyl amide (91 mmoles) was added dropwise. After addition of the allyl amide was complete, 5 μL additional Pt 1,3-divinyltetramethyldisiloxane complex in xylene (3% Pt) was injected into the flask. The resulting liquid was transferred into a distillation flask and 78 g (69% yield) of 91% N-(3-heptamethylcyclotetrasiloxan-yl)propyl-oligohexafluoropropeneoxide-oyl amide (91 mmoles), which corresponds to formula (I) wherein m is 1, n is 3, X is NHC(O), and $R^F$ is given by formula (II) wherein p is 3.2, or more specifically as shown in formula (IX) where R=H and p is an average of 3.2 as determined by gas chromatography, assuming a relative response of individual homologues proportional to their mass and retention times of homologues determined from a monodispersed standard from example 8, with a dispersivity index, $X_w/X_n$, of 1.1. The major impurities in the product were unreacted N-allyl-oligohexafluoropropeneoxide-oyl amides.

EXAMPLE 11

In a 1.5 dram vial containing 1.0 g of 99% [3-(perfluoro-2,5,8,11-tetramethyl-3,6,9,12-tetraoxapentadecanoyl)oxypropyl]-heptamethylcyclotetrasiloxane (0.87 mmoles) was injected 2.0 μL of trifluoromethanesulfonic acid (0.023 mmoles) and the mixture was shaken. The vial was warmed with a heating gun and the viscosity increased over a period of 10 minutes such that a heavy oil, that flowed slowly when the vial was inverted at room temperature, resulted. The oil was warmed again and let stand for 4 hours. Little or no change in the oil was apparent. To the vial was added 0.01 g of MgO (0.2 mequivalents) and the oil warmed with the heating gun to disperse the salt. After the mixture cooled, 1 mL of pentane was added to the vial and the mixture was shaken. Upon settling, two liquid phases and a solid phase were apparent. The liquid layers were filtered from the solid using a 3 mL syringe equipped with a 0.45 micron filter into a 3 dram vial. The 1.5 dram vial and syringe were rinsed with pentane and the liquid injected through the filter into the 3 dram vial such that an approximately 20% by volume perfluoroethersiloxane mixture in pentane resulted.

The two phases were dispersed by shaking and immediately a 3 μL sample was drawn into a syringe and injected into a gas chromatograph. Signals were observed in the chromatographic trace which had a pattern of four groups of signals. The two groups with the shorter retention time each displayed four narrow well resolved signals which decreased in intensity with increasing retention time. The latter two groups displayed many poorly resolved signals. The retention times of the first group were identical to that of octamethylcyclotetrasiloxane, decamethylcyclopentasiloxane, dodecamethylcyclohexasiloxane, and tetradecamethylcycloheptasiloxane. The largest peak of the second group had the retention time of [3-(perfluoro- 2,5,8,11-tetramethyl-3,6,9,12-tetraoxa-pentadecanoyl)oxypropyl] heptamethylcyclotetrasiloxane. Since a complete redistribution of the siloxane units should result during polymerization, the molar ratio of octamethylcyclotetrasiloxane:decamethylcyclopentasiloxane should equal $K_4/K_4:K_5(0.75)/K_4:K_6(0.75)^2/K_4$ for random placement of siloxane units where the dimethylsiloxane units constitute 75% of all siloxane units in the copolymer and polymerization has resulted in a high molecular weight copolymer. Assuming a molar response factor for the homologues in the gas chromatographic trace which is proportional to the molecular weight the homologue, the observed molar ratio of octamethylcyclotetrasiloxane:decamethylcyclopentasiloxane of 10:4:1 agreed with the theoretical ratio of 10:4:1. The second group consisted of [3-(perfluoro-2,5,8,11-tetramethyl-3,6,9,12-tetraoxapentadecan-oyl)oxypropyl]-heptamethylcyclotetra-siloxane, [3-(perfluoro-2,5,8,11-tetramethyl-3,6,9,12-tetraoxa-pentadecan-oyl)oxypropyl] nonamethylcyclopentasiloxane, [3-(per-fluoro-2,5,8,11-tetramethyl-3,6,9,12-tetraoxapentadecan-oyl)oxy-propyl] undecamethylcyclohexasiloxane, and [3-(perfluoro-2,5,8,11-tetramethyl-3,6,9,12-tetraoxapentadecan-oyl)oxypropyl] tridecamethylcycloheptasiloxane. The molar ratio of [3-(perfluoro-2,5,8,11-tetramethyl-3,6,9,12-tetraoxapentadecan-oyl)oxypropyl] heptamethylcyclotetrasiloxane:[3-(perfluoro-2,5,8,11-tetramethyl-3,6,9,12-tetraoxapentadecan-oyl)oxypropyl] nonamethylcyclopentasiloxane:[3-(perfluoro-2,5,8,11-tetramethyl-3,6,9,12-tetraoxapentadecan-oyl)oxypropyl] undecamethylcyclohexa-siloxane was observed to be 10:5:2 in the gas chromatographic trace which agreed with the theoretical 10:5:2 ratio from $K_4/K_4:1.25K_5(0.75)/K_4:1.5K_6(0.75)^2/K_4$. The match of these ratios confirmed that complete and random redistribution occurred and that a high molecular weight copolymer was formed.

The upper layer was drawn from the lower layer using a syringe and placed in a scintillation vial. An additional 3 mL of pentane was added to the 3 dram vial containing the lower layer and the vial shaken. The top layer was again removed via a syringe and placed in the scintillation vial. Evaporation of the pentane from the solution in the scintillation vial under a stream of nitrogen at room temperature resulted in 0.2 g of an oil which was indistinguishable in a gas chromatographic trace from that of the original dispersion with the exception that the signal from pentane was nearly gone, the signals for octamethylcyclotetrasiloxane and decamethylcyclopentasiloxane were diminished significantly, and the signal for dodecamethylcyclohexasiloxane was slightly reduced relative to the peak for [3-(perfluoro-2,5,8,11-tetramethyl-3,6,9,12-tetraoxapentadecan-oyl)oxypropyl] heptamethylcyclotetra-siloxane.

A gas chromatographic trace of the lower layer in the 3 dram vial displayed almost no signals from the equilibrium cyclosiloxanes. The pentane swelling the copolymer was removed by heating the vial on a hot plate while passing a stream of nitrogen over the surface. This resulted in 0.6 g of a gum which displayed no flow upon cooling when the vial was placed on its side for a period of 2 hours, indicating that the molecular weight of the copolymer was high.

EXAMPLE 12

Into a 1.5 dram vial containing 1.0 g of >99% N-(3-heptamethylcyclotetrasiloxan-yl)propyl-N-methyl-perfluoro-2,5,8-trimethyl-3,6,9-trioxadodecanamide (0.87 mmoles) was injected 2.0 μL of trifluoromethanesulfonic acid (0.023 mmoles) and the mixture was shaken. The vial was warmed with a heating gun and the viscosity increased over a period of 10 minutes such that a heavy oil, that flowed slowly when the vial was inverted at room temperature, resulted. The oil was warmed again and let stand for 4 hours. The resulting viscous linear-cyclic mixture was similar in nature to that which resulted from the polymerization of 99% [3-(perfluoro-2,5,8,11-tetramethyl-3,6,9,12-tetraoxapentadecan-oyl)-oxypropyl] heptamethylcyclotetrasiloxane in Example 11.

EXAMPLE 13

Into a 1.5 dram vial containing 1.0 g of >99% N-(3-heptamethylcyclotetrasiloxan-yl)propyl-perfluoro-2,5,8-trimethyl-3,6,9-trioxadodecanamide (0.87 mmoles) was injected 2.0 μL of trifluoromethanesulfonic acid (0.023 mmoles) and the mixture was shaken. The vial was warmed with a heating gun and the viscosity increased over a period of 10 minutes such that a heavy oil, that displayed almost no flow when the vial was inverted at room temperature, resulted. The oil was warmed again and let stand for 4 hours. A viscous linear-cyclic mixture resulted that was much more viscous than the mixture from the polymerization of 99% [3-(perfluoro-2,5,8,11-tetramethyl-3,6,9,12-tetraoxapentadecanoyl)-oxypropyl] heptamethylcyclotetrasiloxane in Example 11.

EXAMPLE 14

Into a 1.5 dram vial containing 2.0 g of [3-(oligohexafluoropropeneoxide-oyl)oxypropyl] heptamethylcyclotetrasiloxane (1.7 mmoles) from Example 5 was injected 3.0 μL of trifluoromethanesulfonic acid (0.035 mmoles) and the mixture was shaken. The vial was warmed with a heating gun and the viscosity increased over a period of 10 minutes such that a heavy oil, that flowed slowly when the vial was inverted at room temperature, resulted. The oil was warmed again and let stand for 4 hours. To the mixture was added 0.021 of MgO (0.52 mmoles) and the mixture warmed with a heating gun to aid in mixing of the powder. A linear-cyclic mixture, similar in nature to that which resulted from the polymerization of 99% [3-(perfluoro-2,5,8,11-tetramethyl-3,6,9,12-tetraoxapentadecan-oyl)oxypropyl] heptamethylcyclotetrasiloxane in Example 11, was observed by gas chromatographic analysis.

EXAMPLE 15

Into a 1.5 dram vial containing 2.0 g of N-(3-heptamethylcyclotetrasiloxan-yl)propyl-oligohexafluoropropeneoxide-oyl amide (1.7 mmoles) from Example 10 was injected 3.0 μL of trifluoromethanesulfonic acid (0.035 mmoles) and the mixture was shaken. The vial was warmed with a heating gun and the viscosity increased over a period of 10 minutes such that a heavy oil, that displayed almost no flow when the vial was inverted at room temperature, resulted. The oil was warmed again and let stand for 24 hours. The mixture became hazy in appearance at room temperature but became clear upon warming. To the mixture was added 0.012 of MgO (0.30 mmoles) and the mixture warmed with a heating gun to aid in mixing of the powder. A linear-cyclic mixture, similar in nature to that which resulted from the polymerization of 99% [3-(perfluoro-2,5,8,11-tetramethyl-3,6,9,12-tetraoxapentadecan-oyl)oxypropyl] heptamethylcyclotetrasiloxane in Example 11, was observed by gas chromatographic analysis.

EXAMPLE 16

Into a 1.5 dram vial containing 2.0 g of N-(3-heptamethylcyclotetrasiloxan-yl)propyl-oligohexafluoropropeneoxide-oyl amide (1.7 mmoles) from Example 10 was injected 19.0 μL of tetrabutylammonium fluoride in tetrahydrofuran (0.019 mmoles) and the mixture was shaken. The vial was warmed gently with a heating gun over a period of 10 minutes. After cooling to room temperature, a viscous mixture was noted. The heating of the vial was repeated 6 times until a heavy oil, that displayed very slow flow when the vial was inverted at room temperature, resulted and no apparent increase in viscosity was observed upon subsequent heating. The oil was warmed again and let stand for 24 hours. The mixture remained clear in appearance at room temperature. The vial was then heated strongly with the formation of bubbles, presumably from the decomposition of the tetrabutylammonium salt with the liberation of tributylamine and butene. A linear-cyclic mixture, similar in nature to that which resulted in Example 15 was observed by gas chromatographic analysis.

EXAMPLE 17

A 3-necked 50 mL round bottom flask was equipped with a magnetic stirring bar, a condenser, and a temperature probe. The flask was charged with 10.0 g of 1H,1H,2H-perfluoro-1-octene (28.9 mmoles) and 10.0 g of heptamethylcyclotetrasiloxane (35.4 mmoles). The mixture was heated to 90° C. and 5 μL of a Pt 1,3-divinyltetra-methyldisiloxane complex in xylene (3% Pt) was added via a syringe. An exothermic reaction occurred with a rapid increase in temperature to 130° C. which cooled after 3 minutes. A gas chromatographic analysis indicated a low conversion to a single product. The addition of 20 μL of the 1,3-divinyltetramethyldisiloxane complex (3% Pt) did not result in higher conversion. The contents of the flask were distilled at 80° C. and <2 mmHg to yield a fraction of 4.2 g (23% yield) of (6.7 mmoles), which corresponds to formula (I) wherein m is 1, n is 1, X is $CH_2$ and $R^F$ is a perfluorinated straight chain monovalent alkyl radical of 6 carbon atoms, or more specifically as shown in formula (X) below where q=5. The product was analyzed by spectroscopy with the following results: H NMR 400 MHz, $CDCl_3$: d 0.1 (m 21 H), 0.8 (m 2 H), 2.1 (m 2 H); IR (neat liquid on NaCl): $cm^{-1}$: 2970 (m), 2870 (w), 1445 (w), 1405 (w), 1370 (w), 1265 (s), 1240 (s), 1205 (m), 1175 (w), 1150 (m), 990 (vs), 810 (vs).

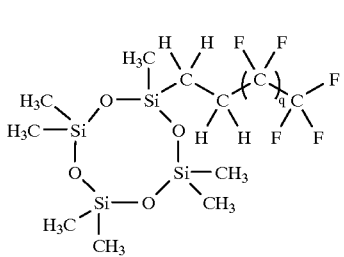

(X)

EXAMPLE 18

Into a 1.5 dram vial containing 2.0 g of 99% 1H,1H,2H,2H,1-(heptamethylcyclotetrasiloxan-yl)-perfluorooctane (3.2 mmoles) from Example 17 was injected 3.0 μL of trifluoromethanesulfonic acid (0.035 mmoles) and the mixture was shaken. The vial was warmed with a heating gun and the viscosity increased over a period of 10 minutes such that a gum, which displayed almost no flow when the vial was inverted at room temperature, resulted. The gum was warmed again and let stand for 24 hours. To the vial was added 0.021 g of MgO (0.52 mmoles) and the mixture warmed with a heating gun to aid in the dispersion of the powder. A linear-cyclic mixture, similar in nature to that which resulted from the polymerization of 99% [3-(perfluoro-2,5,8,11-tetramethyl-3,6,9,12-tetraoxapentadecanoyl)oxypropyl] heptamethylcyclotetrasiloxane in Example 11, was observed by gas chromatographic analysis.

EXAMPLE 19

Into a 1.5 dram vial containing 0.20 g of 99% [3-(perfluoro-2,5,8,11-tetramethyl-3,6,9,12-tetraoxapentadecanoyl)oxypropyl] heptamethylcyclotetrasiloxane (0.18 mmoles) from Example 2 and 9.5 g of octamethylcyclotetrasiloxane (32.0 mmoles) was injected 15 µL of trifluoromethanesulfonic acid (0.17 mmoles) and the mixture was shaken. The vial was warmed with a heating gun and the viscosity increased over a period of 10 minutes such that a gum, which displayed almost no flow when the vial was inverted at room temperature, resulted. The gum was warmed again and let stand for 24 hours. To the vial was added 0.1 g of MgO (2.5 mmoles) and the mixture warmed with a heating gun to aid in dispersion of the powder. A linear-cyclic mixture resulted which was observed by gas chromatographic analysis. Since a complete redistribution of the siloxane units should result during polymerization, the molar ratio of octamethylcyclotetrasiloxane:decamethylcyclopentasiloxane:dodecamethylcyclohexasiloxane should equal $K_4/K_4:K_5(0.997)/K_4:K_6(0.997)^2/K_4$ for random placement of siloxane units where the dimethylsiloxane units constitute 99.7% of all siloxane units in the copolymer and polymerization has resulted in a high molecular weight copolymer. Assuming a molar response factor for the homologues in the gas chromatographic trace which is proportional to the molecular weight of the homologue, the observed molar ratio of octamethylcyclotetrasiloxane:decamethylcyclopentasiloxane:dodecamethylcyclohexasiloxane of 10:5.1:1.3 agreed well with the theoretical ratio of 10:5.2:1.8. The mole ratio of octamethylcyclotetrasiloxane:[3-(perfluoro-2,6,8,11-tetramethyl-3,6,9,12-tetraoxapentadecanoyl)oxypropyl] heptamethylcyclotetrasiloxane was determined to be 100:2 which agreed well with the theoretical ratio of 100:1.2 from the relationship $K_4(0.997)^4:4K_4(0.997)^3(0.003)$ for a random polymerization to high molecular weight.

EXAMPLE 20

Into a 1.5 dram vial containing 0.20 g of 99% [3-(perfluoro-2,5,8,11,14-pentamethyl-3,6,9,12,15-pentaoxapentadecan-oyl)oxypropyl] heptamethylcyclotetrasiloxane (0.17 mmoles), 1.90 g of octamethylcyclotetrasiloxane (6.4 mmoles) and 0.020 g of 1,3,5,7-tetravinyltetramethylcyclotetrasiloxane (0.006 mmoles) was injected 3 µL of trifluoromethanesulfonic acid (0.03 mmoles) and the mixture was shaken. The vial was warmed gently with a heating gun and the viscosity increased over a period of 30 minutes. The mixture was warmed again and let stand for 24 hours. To the vial was added 0.02 g of MgO (0.4 mmoles) and the mixture warmed with a heating gun to aid in dispersion of the powder. A linear-cyclic mixture resulted which was dissolved in 6 mL of cyclohexane and analyzed by gas chromatography. Since a compete redistribution of the siloxane units should result during polymerization, the molar ratio of octamethylcyclotetrasiloxane:decamethylcyclopentasiloxane:dodecamethylcyclohexasiloxane should equal $K_4/K_4:K_5(0.993)/K_4:K_6(0.993)^2/K_4$ for random placement of siloxane units where the dimethylsiloxane units constitute 99.3% of all siloxane units in the copolymer and polymerization has resulted in a high molecular weight copolymer. Assuming a molar response factor for the homologues in the gas chromatographic trace which is proportional to the molecular weight of the homologue, the observed molar ratio of octamethylcyclotetrasiloxane:decamethylcyclopentasiloxane:dodecamethylcyclohexasiloxane of 10:5.5:1.7 agreed well with the theoretical ratio of 10:5.2:1.8. Small peaks were observed in gas chromatographic trace which had retention times for that of vinylheptamethylcyclotetrasiloxane and vinylnonamethylcyclopentasiloxane indicating that the methylvinylsiloxane units from the 1,3,5,7-tetravinyltetramethylcyclotetrasiloxane were randomly dispersed through the copolymer and cyclic oligomers.

EXAMPLE 21

Into a 1.5 dram vial containing 0.15 g of 94% [3-(perfluoro-2,5-dimethyl-3,6-dioxanonan-oyl)oxypropyl] heptamethylcyclotetrasiloxane (0.17 mmoles), 2.15 g of octamethylcyclotetrasiloxane (7.2 mmoles) and 0.033 g of 1,3-divinyl-1,1,3,3-tetramethyldisiloxane (0.15 mmoles) was injected 3 µL of trifluoromethanesulfonic acid (0.03 mmoles) and the mixture was shaken. The vial was warmed with a heating gun and the viscosity increased over a period of 10 minutes. To the vial was added 0.05 g of MgO (1 mmole). A copolymer-cyclic mixture was dissolved in 3 mL of cyclohexane and analyzed by gas chromatography. Since a complete redistribution of the siloxane units should result during polymerization, the molar ratio of octamethylcyclotetrasiloxane:decamethylcyclopentasiloxane:dodecamethylcyclohexasiloxane should equal $K_4/K_4:K_5(0.994)/K_4:K_6(0.994)^2/K_4$ for random placement of siloxane units where the dimethylsiloxane units constitute 99.4% of all siloxane units in the copolymer and polymerization has resulted in a high molecular weight copolymer as a macromolecule with a degree of polymerization of approximately 200 was targeted by the proportions of cyclosiloxanes to disiloxanes used. Assuming a molar response factor for the homologues in the gas chromatographic trace which is proportional to the molecular weight of the homologue, the observed molar ratio of octamethylcyclotetrasiloxane:decamethylcyclopentasiloxane:dodecamethylcyclohexasiloxane of 10:6.4:2.1 agreed with the theoretical ratio of 10:5.2:1.8. No unreacted 1,3-divinyl-1,1,3,3-tetramethyldisiloxane was observed in the gas chromatographic trace.

The present invention may be embodied in other specific forms without departing from the spirit of essential attributes thereof, and accordingly, reference should be made to the appended claims, rather than to the foregoing specification, as indicating the scope of the invention.

The above-referenced patents and publications are hereby incorporated by reference.

We claim:

1. A polymerizable cyclosiloxane having one substituent comprising a perfluorinated organic moiety, said cyclosiloxane having the general formula (I)

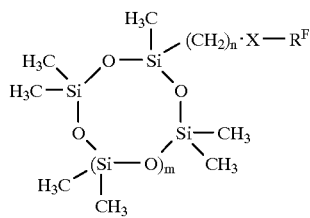

(I)

wherein m is an integer of 1 to 12;

n is an integer of 1 to 4;

X is a divalent radical selected from the group consisting of O, NH, N(CH$_3$), OC(O), NHC(O), N(CH$_3$)C(O), and CH$_2$; and R$^F$ comprises a perfluorinated straight chain or branched chain monovalent alkyl radical of 1 to 25 carbon atoms; or R$^F$ is a perfluorinated ether radical of the general formula (II):

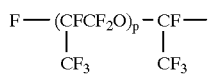

(II)

wherein p is an integer of 1 to 10.

2. A polymerizable cyclosiloxane as defined in claim 1 wherein m is 1 or 2.

3. A polymerizable cyclosiloxane as defined in claim 2 wherein n is 3 and X is OC(O).

4. A polymerizable cyclosiloxane as defined in claim 3 wherein R$^F$ is a perfluorinated ether radical of the general formula (II) wherein p is 1 to 5.

5. A polymerizable cyclosiloxane as defined in claim 3 wherein R$^F$ is a perfluorinated straight chain alkyl radical of 2 to 10 carbon atoms.

6. A polymerizable cyclosiloxane as defined in claim 2 wherein n is 3 and X is NHC(O).

7. A polymerizable cyclosiloxane as defined in claim 6 wherein R$^F$ is a perfluorinated ether radical of the general formula (II) wherein p is 1, to 5.

8. A polymerizable cyclosiloxane as defined in claim 6 wherein R$^F$ is a perfluorinated straight chain alkyl radical of 2 to 10 carbon atoms.

9. A polymerizable cyclosiloxane as defined in claim 2 wherein n is 3 and X is N(CH$_3$)C(O).

10. A polymerizable cyclosiloxane as defined in claim 9 wherein R$^F$ is a perfluorinated ether radical of the general formula (II) wherein p is 1 to 5.

11. A polymerizable cyclosiloxane as defined in claim 9 wherein R$^F$ is a perfluorinated straight chain alkyl radical of 2 to 10 carbon atoms.

12. A polymerizable cyclosiloxane as defined in claim 2 wherein n is 1 and X is CH$_2$.

13. A polymerizable cyclosiloxane as defined in claim 12 wherein R$^F$ is a perfluorinated straight chain alkyl radical of 2 to 10 carbon atoms.

14. A polymerizable cyclosiloxane as defined in claim 12 wherein R$^F$ is a perfluorinated ether radical of the general formula (II) wherein p is 1 to 5.

15. A copolymer of the general formula:

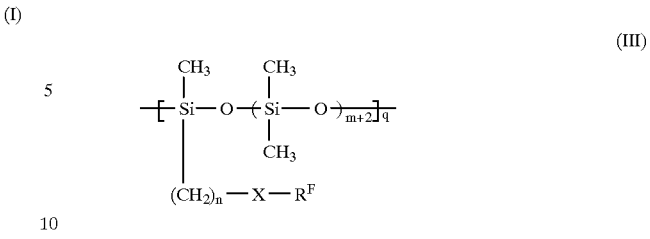

(III)

wherein each m is independently an integer of 1 to 12, each n is independently an integer of 1 to 4, each X is independently a divalent radical selected from the group consisting of O, NH, N(CH$_3$), OC(O), NHC(O), N(CH$_3$)C(O), or CH$_2$; each R$^F$ is independently either a perfluorinated straight chain or branched chain monovalent alkyl radical of 1 to 25 carbon atoms or a perfluorinated ether radical of the general formula (II):

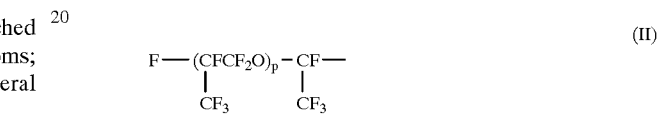

(II)

wherein p is an integer of 1 to 10; and q is from 2 to about 1,000,000.

16. A copolymer as defined in claim 15 prepared by the ring-opening polymerization of polymerizable cyclosiloxanes having one substituent comprising a perfluorinated organic moiety, said cyclosiloxanes having the general formula (I)

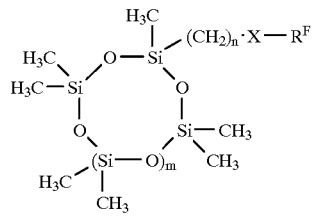

(I)

wherein m is an integer of 1 to 12;

n is an integer of 1 to 4;

X is a divalent radical selected from the group consisting of O, NH, N(CH$_3$), OC(O), NHC(O), N(CH$_3$)C(O), and CH$_2$; and R$^F$ comprises a perfluorinated straight chain or branched chain monovalent alkyl radical of 1 to 25 carbon atoms; or R$^F$ is a perfluorinated ether radical of the general formula (II):

(II)

wherein p is an integer of 1 to 10.

17. A copolymer prepared by the ring-opening polymerization of polymerizable cyclosiloxanes as defined in claim 16 wherein n is 3, X is OC(O), and R$^F$ is a perfluorinated ether radical of the general formula (II) wherein p is 1 to 5.

18. A copolymer prepared by the ring-opening polymerization of polymerizable cyclosiloxanes as defined in claim 16 wherein n is 3, X is OC(O), and $R^F$ is a perfluorinated straight chain alkyl radical of 2 to 10 carbon atoms.

19. A copolymer prepared by the ring-opening polymerization of polymerizable cyclosiloxanes as defined in claim 16 wherein n is 3, X is NHC(O) and R is a perfluorinated ether radical of the general formula (II) wherein p is 1 to 5.

20. A copolymer prepared by the ring-opening polymerization of polymerizable cyclosiloxanes as defined in claim 16 wherein n is 3, X is NHC(O) and $R^F$ is a perfluorinated straight chain alkyl radical of 2 to 10 carbon atoms.

21. A copolymer prepared by the ring-opening polymerization of polymerizable cyclosiloxanes as defined in claim 16 wherein n is 3, X is $N(CH_3)C(O)$ and $R^F$ is a perfluorinated ether radical of the general formula (II) wherein p is 1 to 5.

22. A copolymer prepared by the ring-opening polymerization of polymerizable cyclosiloxanes as defined in claim 16 wherein n is 3, X is $N(CH_3)C(O)$ and $R^F$ is a perfluorinated straight chain alkyl radical of 2 to 10 carbon atoms.

23. A copolymer prepared by the ring-opening polymerization of polymerizable cyclosiloxanes as defined in claim 16 wherein n is 1, X is $CH_2$ and $R^F$ is a perfluorinated straight chain alkyl radical of 2 to 10 carbon atoms.

24. A copolymer prepared by the ring-opening polymerization of polymerizable cyclosiloxanes as defined in claim 16 wherein n is 1, X is $CH_2$ and $R^F$ is a perfluorinated ether radical of the general formula (II) wherein p is 1 to 5.

25. A copolymer prepared by the copolymerization of
(a) polymerizable cyclosiloxanes having one substituent comprising a perfluorinated organic moiety, said cyclosiloxane having the general formula (I)

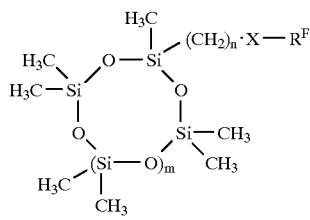

(I)

wherein
m is an integer of 1 to 12;
n is an integer of 1 to 4;
X is a divalent radical selected from the group consisting of O, NH, $N(CH_3)$, OC(O), NHC(O), $N(CH_3)C(O)$, and $CH_2$; and
$R^F$ comprises a perfluorinated straight chain or branched chain monovalent alkyl radical of 1 to 25 carbon atoms; or $R^F$ is a perfluorinated ether radical of the general formula (II):

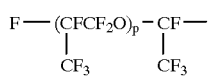

(II)

wherein
p is an integer of 1 to 10; and
(b) a copolymerization substituent selected from the group consisting of cyclodimethylsiloxanes, polydimethylsiloxanes and mixtures thereof;

whereby said copolymer contains a lesser proportion of fluorinated siloxane groups than the cyclosiloxanes of formula (I).

26. A copolymer as defined in claim 25 prepared by the ring-opening polymerization of (a) said polymerizable cyclosiloxanes wherein n is 3, X is OC(O) and $R^F$ is a perfluorinated ether radical of the general formula (II) wherein p is 1 to 5; and (b) octamethylcyclotetrasiloxane or decamethylcyclopentasiloxane.

27. A copolymer as defined in claim 25 prepared by the ring-opening polymerization of (a) said polymerizable cyclosiloxanes wherein n is 3, X is OC(O) and $R^F$ is a perfluorinated straight chain alkyl radical of 2 to 10 carbon atoms; and (b) octamethylcyclotetrasiloxane or decamethylcyclopentasiloxane.

28. A copolymer as defined in claim 25 prepared by the ring-opening polymerization of (a) said polymerizable cyclosiloxanes wherein n is 3, X is NHC(O), and $R^F$ is a perfluorinated ether radical of the general formula (II) wherein p is 1 to 5; and (b) octamethylcyclotetrasiloxane or decamethylcyclopentasiloxane.

29. A copolymer as defined in claim 25 prepared by the ring-opening polymerization of (a) said polymerizable cyclosiloxanes wherein n is 3, X is NHC(O) and $R^F$ is a perfluorinated straight chain alkyl radical of 2 to 10 carbon atoms; and (b) octamethylcyclotetrasiloxane or decamethylcyclopentasiloxane.

30. A copolymer as defined in claim 25 prepared by the ring-opening polymerization of (a) said polymerizable cyclosiloxanes wherein n is 3, X is $N(CH_3)C(O)$ and $R^F$ is a perfluorinated ether radical of the general formula (II) wherein p is 1 to 5; and (b) octamethylcyclotetrasiloxane or decamethylcyclopentasiloxane.

31. A copolymer as defined in claim 25 prepared by the ring-opening polymerization of (a) said polymerizable cyclosiloxanes wherein n is 3, X is $N(CH_3)C(O)$ and $R^F$ is a perfluorinated straight chain alkyl radical of 2 to 10 carbon atoms; and (b) octamethylcyclotetrasiloxane or decamethylcyclopentasiloxane.

32. A copolymer defined in claim 25 prepared by the ring-opening polymerization of (a) said polymerizable cyclosiloxanes wherein n is 1, X is $CH_2$ and $R^F$ is a perfluorinated straight chain alkyl radical of 2 to 10 carbon atoms; and (b) octamethylcyclotetrasiloxane or decamethylcyclopentasiloxane.

33. A copolymer as defined in claim 25 prepared by the ring-opening polymerization of (a) said polymerizable cyclosiloxanes wherein n is 1, X is $CH_2$ and $R^F$ is a perfluorinated ether radical of the general formula (II) wherein p is 1 to 5; and (b) octamethylcyclotetrasiloxane or decamethylcyclopentasiloxane.

34. A copolymer as defined in claim 15 wherein said copolymer further comprises other siloxy repeating units which are selected from the group consisting of methylhydrogensiloxy, methylvinylsiloxy, methylphenylsiloxy, methylcyanoethylsiloxy, hydroxypropylsiloxy, aminopropylmethylsiloxy, trifluoropropylmethylsiloxy, mixtures of any of the foregoing and the like.

35. A copolymer as defined in claim 25 wherein said copolymer further comprises other siloxy repeating units which are selected from the group consisting of methylhydrogensiloxy, methylvinylsiloxy, methylphenylsiloxy, methylcyanoethylsiloxy, hydroxypropylsiloxy, aminopropylmethylsiloxy, trifluoropropylmethylsiloxy, mixtures of any of the foregoing and the like.

36. A copolymer as defined in claim 16 wherein said polymerization is controlled by capping said copolymer at both ends by equilibrating said cyclosiloxane with an end-capping agent selected from the group of a disiloxane, a disiloxane equivalent incorporated into a small polysiloxane and mixtures thereof.

37. A copolymer as defined in claim 25 wherein said polymerization is controlled by capping said copolymer at both ends by equilibrating said cyclosiloxane with an end-capping agent selected from the group of a disiloxane, a disiloxane equivalent incorporated into a small polysiloxane and mixtures thereof.

38. A copolymer as defined in claim 34 wherein said polymerization is controlled by capping said copolymer at both ends by equilibrating said cyclosiloxane with an end-capping agent selected from the group of a disiloxane, a disiloxane equivalent incorporated into a small polysiloxane and mixtures thereof.

39. A copolymer as defined in claim 35 wherein said polymerization is controlled by capping said copolymer at both ends by equilibrating said cyclosiloxane with an end-capping agent selected from the group of a disiloxane, a disiloxane equivalent incorporated into a small polysiloxane and mixtures thereof.

40. A cyclosiloxane of the formula (V):

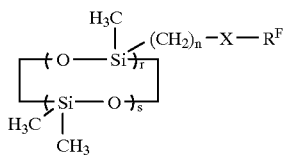

(V)

wherein
n is an integer of 1 to 4,
X is a divalent radical selected from the group consisting of O, NH, N(CH$_3$), OC(O), NHC(O), N(CH$_3$)C(O) CH$_2$; and
R$^F$ is a perfluorinated straight chain or branched chain monovalent alkyl radical of 1 to 25 carbon atoms, or R$^F$ is a perfluorinated ether radical of the general formula (II):

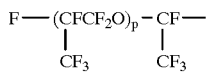

(II)

wherein
p is an integer of 1 to 10;
r is 1 to t;
s s is t minus r; and
t is 4 to 20.

* * * * *

UNITED STATES PATENT AND TRADEMARK OFFICE
CERTIFICATE OF CORRECTION

PATENT NO.   : 5,914,420
DATED        : June 22, 1999
INVENTOR(S)  : Mark A. Buese et al.

It is certified that error appears in the above-indentified patent and that said Letters Patent is hereby corrected as shown below:

Title page, item [54] should read as follows:

PERFLUORINATED ORGANO SUBSTITUTED CYCLOSILOXANES AND COPOLYMERS PREPARED FROM THESE CYCLOSILOXANES

Column 1, line 2 and 4, rewrite "CYYLOSILOXANES" to read "CYCLOSILOXANES"

Title page:

On column 1, line 4 rewrite "CYCLOSILOXAHES" to read "CYCLOSILOXANES"

Signed and Sealed this

Ninth Day of November, 1999

Attest:

Attesting Officer

Q. TODD DICKINSON

Acting Commissioner of Patents and Trademarks